US008257291B2

(12) United States Patent
Kazerooni et al.

(10) Patent No.: US 8,257,291 B2
(45) Date of Patent: Sep. 4, 2012

(54) EXTERNAL WALKING ASSIST DEVICE FOR THOSE WITH LOWER LEG INJURIES

(75) Inventors: Homayoon Kazerooni, Berkeley, CA (US); Sara Marie Haislip, Portland, OR (US); Jonathan Ames, Emeryville, CA (US); Esha Datta, West Hills, CA (US)

(73) Assignee: The Regents of the University of California, Oakland, CA (US)

( * ) Notice: Subject to any disclaimer, the term of this patent is extended or adjusted under 35 U.S.C. 154(b) by 532 days.

(21) Appl. No.: 12/483,183

(22) Filed: Jun. 11, 2009

(65) Prior Publication Data

US 2010/0010641 A1 Jan. 14, 2010

Related U.S. Application Data

(60) Provisional application No. 61/060,791, filed on Jun. 11, 2008.

(51) Int. Cl.
*A61F 5/00* (2006.01)

(52) U.S. Cl. ........................................ 602/16; 602/19

(58) Field of Classification Search ................ 602/5, 16, 602/19, 32; 128/882, 881; 623/44, 47
See application file for complete search history.

(56) References Cited

U.S. PATENT DOCUMENTS

| | | | | |
|---|---|---|---|---|
| 2,827,897 | A * | 3/1958 | Pawlowski | 602/16 |
| 4,058,119 | A | 11/1977 | Rosequist | |
| 5,020,790 | A * | 6/1991 | Beard et al. | 482/4 |
| 5,300,016 | A | 4/1994 | Marlatt | |
| 5,913,901 | A * | 6/1999 | Lacroix | 623/47 |
| 6,808,540 | B1 * | 10/2004 | Gramnas | 623/44 |
| 2007/0050044 | A1 * | 3/2007 | Haynes et al. | 623/24 |

FOREIGN PATENT DOCUMENTS

WO WO 99/08645 2/1999

OTHER PUBLICATIONS

The International Search Report and the Written Opinion mailed on Aug. 4, 2009, for International Patent Application No. PCT/US2009/047117, filed Jun. 11, 2009. 10 pages.

* cited by examiner

*Primary Examiner* — Michael A. Brown
(74) *Attorney, Agent, or Firm* — Diederiks & Whitelaw, PLC

(57) ABSTRACT

A walking assist device, which is to be worn on a person's leg, includes a shank link, a thigh member, and a knee mechanism. The thigh member is in contact with the person's thigh when the device is worn on the person's leg. The knee mechanism rotatably connects the shank link to the thigh member. When the shank link is in contact with the ground, the knee mechanism is configured to resist the rotation of the shank link relative to the thigh member to prevent the person's foot from contacting the ground and reduces ground reaction forces entering the person's foot.

33 Claims, 21 Drawing Sheets

EXTERNAL WALKING ASSIST DEVICE FOR THOSE WITH LOWER LEG INJURIES

CROSS-REFERENCE TO RELATED APPLICATIONS

This application claims the benefit of U.S. Provisional Application No. 61/060,791, entitled EXTERNAL HUMAN ASSIST DEVICE FOR THOSE WITH LOWER LEG INJURIES, filed Jun. 11, 2008, which is incorporated herein by reference in its entirety for all purposes.

BACKGROUND

1. Field

The present application relates generally to walking assist devices that assist in walking post-injury.

2. Related Art

Crutches are medical devices used when a person has an injured leg or is otherwise unable to use his or her leg. Conventional crutches generally have a single degree of freedom and two endpoints. One endpoint contacts the ground, while the other makes contact with some part of the person's upper body, such as the underarm, and is held by the user's hand. Conventional crutches function by allowing users to put their weight into the crutches, bypassing the injured leg entirely. There are many different kinds of crutches currently on the market; they vary in quality and ergonomic support, and therefore in price. The two most commonly used types are underarm and forearm crutches.

There are many disadvantages to using conventional crutches. The first disadvantage of using conventional crutches is that one must hold onto them, thereby restricting the use of one's hands for other purposes. It is very difficult to walk, stand up, sit down, open and close doors, and climb stairs using crutches. It takes approximately twice the energy to walk with crutches as to walk without them. (See, Fisher, S. V., Patterson, R P (1981); Energy cost of ambulation with crutches; *Archives of physical medicine and rehabilitation,* 62, 250-56). Conventional crutches depend highly on the user's upper arm strength, which for weak or elderly patients may be a problem. Another problem with conventional crutches is that patients tend to rest their body weight on the axillary pad of the crutch, thereby applying undue pressure. (See, McFall, B., Arya, N., Soong, C., Lee, B. & Hannon, R. (2004); Crutch induced axillary artery injury; *The Ulster Medical Journal,* 73, 50-52). This pressure damages the arteries in the axillary region. (See, Feldman, D., Vujic, I., McKay, D., Callcott, F. & Uflacker, R. (1995); Crutch-induced axillary artery injury; *Journal of Cardiovascular and Interventional Radiology,* 18, 296-99). Nerve damage can also result. (See, "Crutch Fitting and Walking"; *University of North Carolina at Chapel Hill: Campus Health Services;* 2006; <http://campushealth.unc.edu/index.php?option=com_content&task=view&id=102&Itemid=65>).

One technological development that has attempted to replace the crutch, as opposed to redesigning it, is called the "iWALKFree". (See, "iWALKFree High Performance Rehabilitation Device—Hands-free Crutch"; *Health Check Systems;* 2004; <http://www.healthchecksystems.com/i_walk_free.htm>). This device works by being attached to the thigh while resting the knee, in a bent position, on a flat platform. The "iWALKFree" has the advantage of leaving the hands free, but seems to force the leg to stay in a single, awkwardly bent position. The ground reaction forces are transferred away from the foot of the injured leg and directly into the person's knee joint. With the knee bent, the person's center of mass will be shifted backwards, potentially causing instability. Additionally, the iWALKfree does not contain a knee-like joint, giving it zero degrees of freedom. This "peg-leg" type of design causes the user to experience an abnormal and potentially jarring gait cycle. The design of this device leaves much to be improved upon, while its existence suggests that there exists a need for an alternative to crutches.

SUMMARY

In one exemplary embodiment, a walking assist device, which is to be worn on a person's leg, includes a shank link, a thigh member, and a knee mechanism. The thigh member is in contact with the person's thigh when the device is worn on the person's leg. The knee mechanism rotatably connects the shank link to the thigh member. When the shank link is in contact with the ground, the knee mechanism is configured to resist the rotation of the shank link relative to the thigh member to prevent the person's foot from contacting the ground and reduces ground reaction forces entering the person's foot.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF EXEMPLARY EMBODIMENTS

Figure 1:
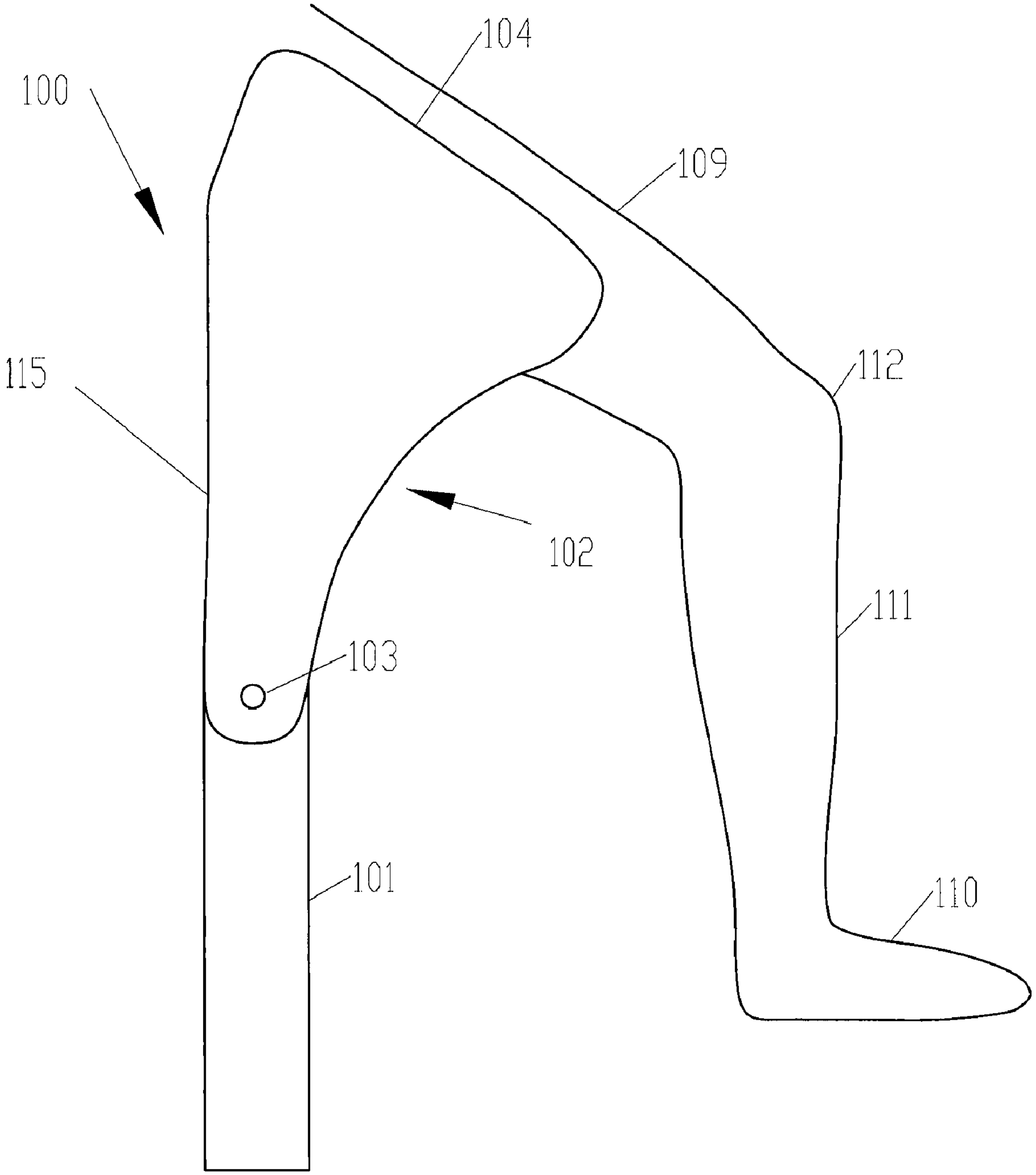
FIGS. 1 and 2 depict an exemplary embodiment of a walking assist device attached to a person's leg.

In accordance with one exemplary embodiment, FIG. 1 is a drawing illustrating a walking assist device 100 having a shank link 101 and a thigh member 102 rotatably connected to each other at a knee mechanism 103. Thigh member 102 is configurable to be in contact with the person's thigh 109. In operation, when walking assist device 100 is in contact with the ground through its shank link 101 (i.e., stance phase), knee mechanism 103 is resisting the motion (i.e., rotation) of shank link 101 relative to thigh member 102, thereby preventing the person's foot 110 from contacting the ground and reducing the ground reaction force entering the person's foot 110.

In some embodiments, as shown in FIG. 1, walking assist device 100 operates such that when shank link 101 is not in contact with the ground (i.e., swing phase), the resistance of knee mechanism 103 to the motion (i.e., rotation) of shank link 101 relative to thigh member 102 is less than the resistance of knee mechanism 103 when shank link 101 is in contact with the ground. This low resistance allows the person to freely swing walking assist device 100 during the swing phase of a walking cycle. In effect, since knee mechanism 103 is rather inflexible to rotation during the stance phase and flexible to rotation during the swing phase, walking assist device 100 behaves like the person's leg, allowing the person to walk without putting his or her foot 110 on the ground.

In some embodiments, said knee mechanism comprises at least one rotary joint allowing rotary motion between shank link 101 and thigh member 102 during the swing phase. In some embodiments, said knee mechanism comprises a four-bar mechanism allowing motion (i.e., rotation) between shank link 101 and thigh member 102 during the swing phase. One experienced in the design of mechanisms can develop various kinds of knee mechanism 103 to create knee-like motion between shank link 101 and thigh member 102.

Figure 2:
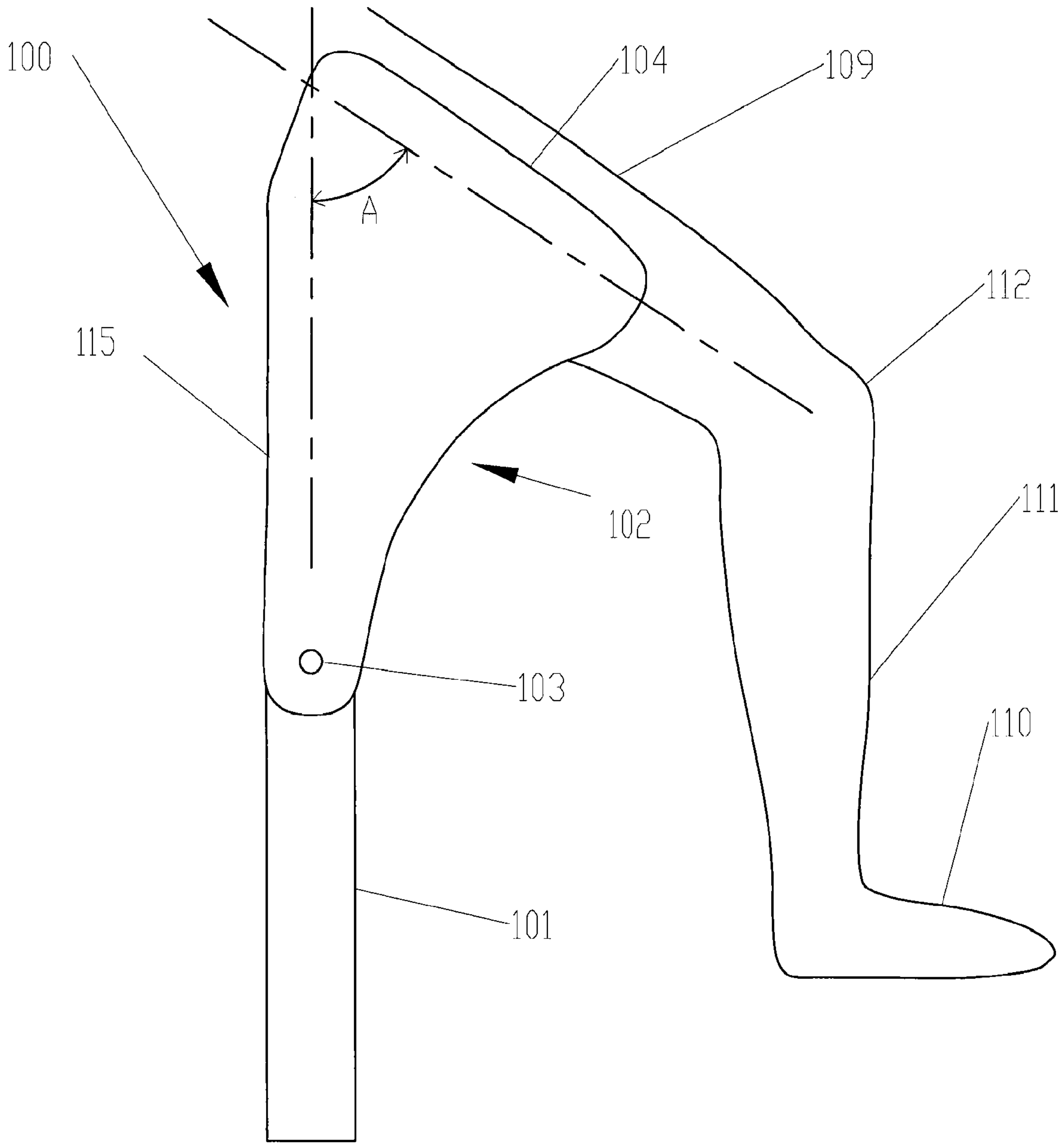
Figure 3:
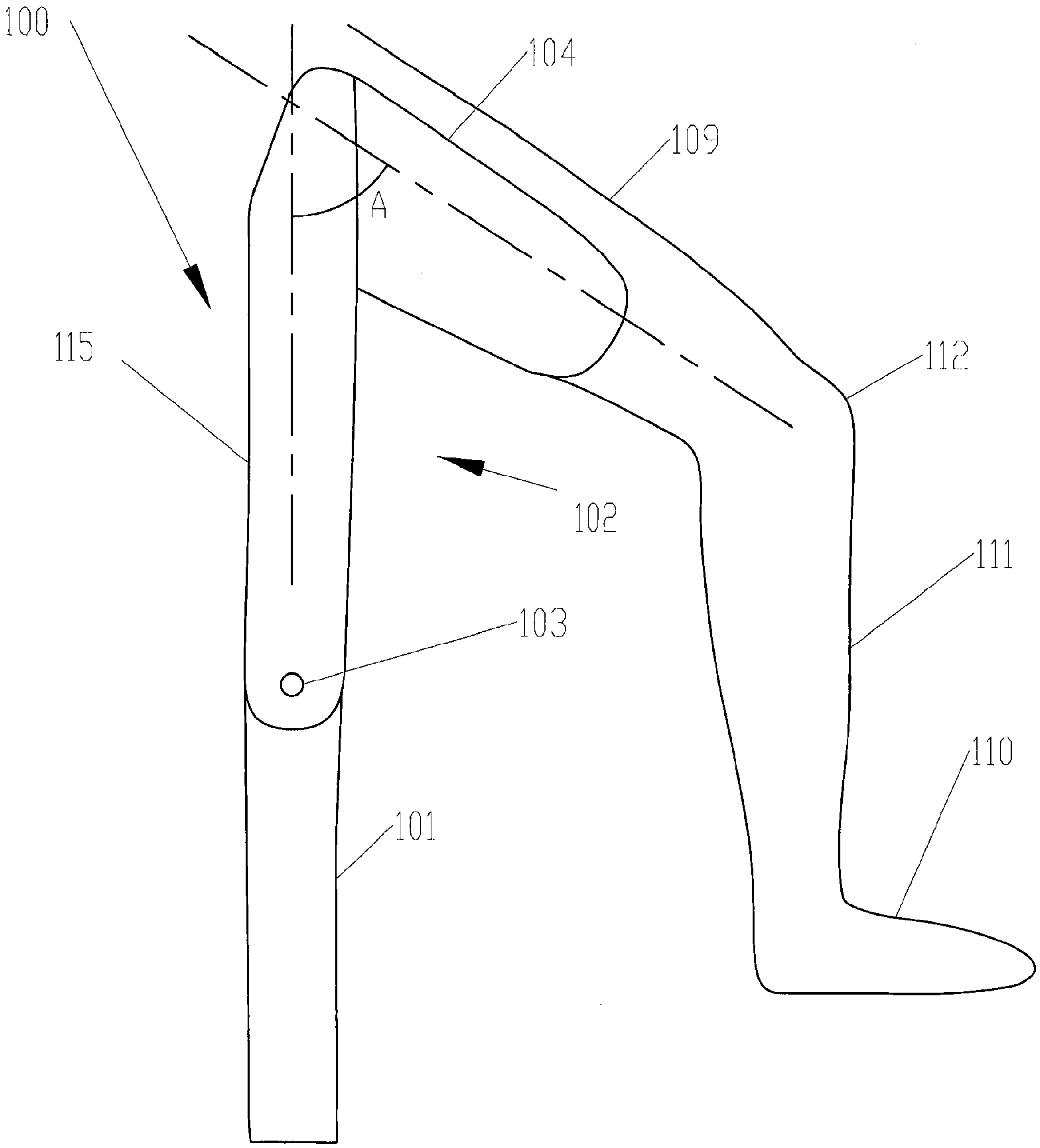
FIG. 3 depicts another embodiment of a walking assist device.

In some embodiments, as shown in FIG. 1, thigh member 102 further comprises a thigh link 115 and a thigh support 104, which is in contact with the person's thigh 109 when walking assist device 100 is worn on the person's leg. In some embodiments, as shown in FIG. 2, the orientation of thigh link 115 relative to thigh support 104 (shown by angle A) is fixed. In particular, as shown in FIG. 3, angle A can be defined between a center line along thigh link 115, which extends through knee mechanism 103, and a center line along thigh support 104, which approximately parallels a center line along the person's thigh 109. In some embodiments, the orientation of thigh link 115 relative to thigh support 104 is adjustable, which helps the person to find the most comfortable fit during walking.

Figure 4:
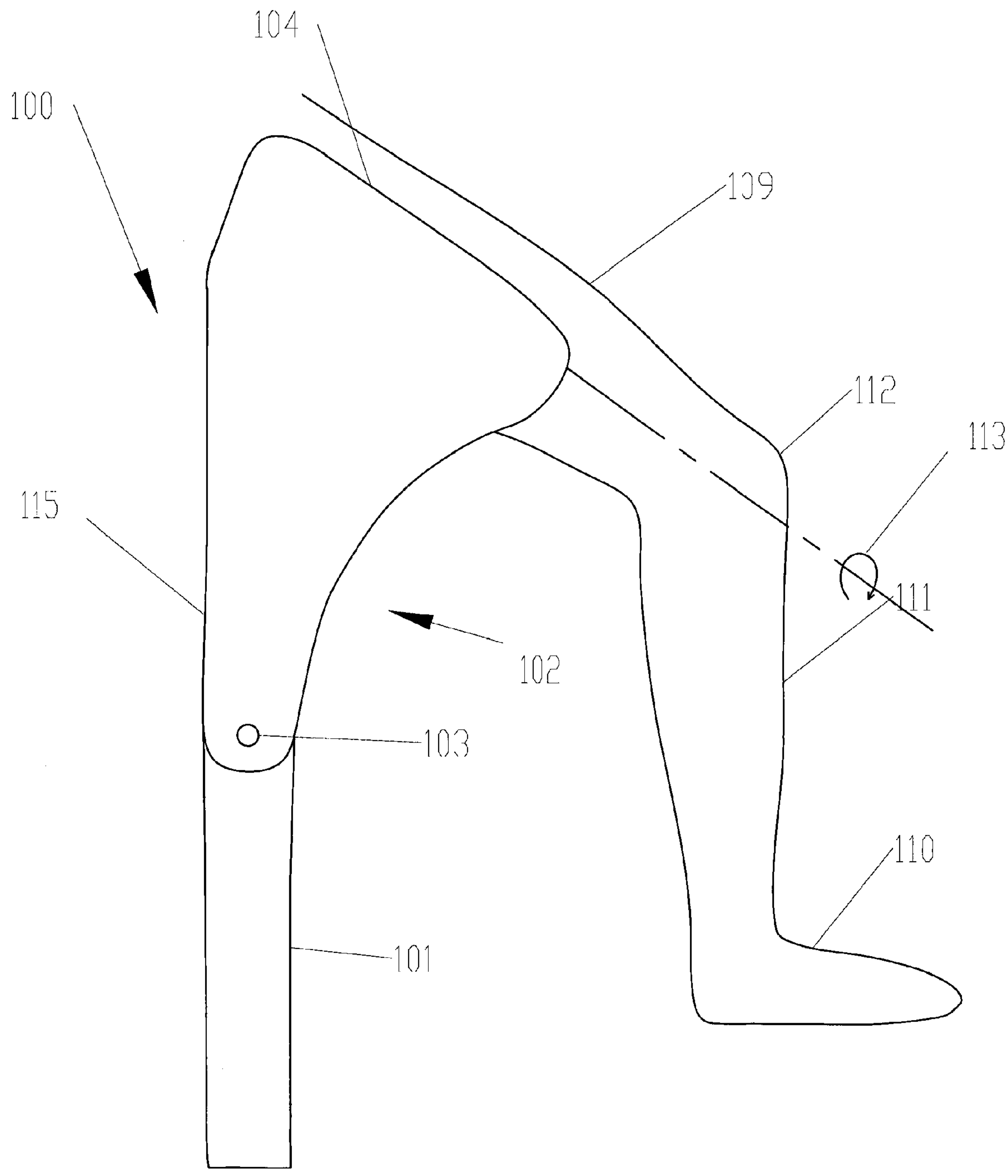
FIG. 4 depicts another embodiment of a walking assist device.
Figure 5:
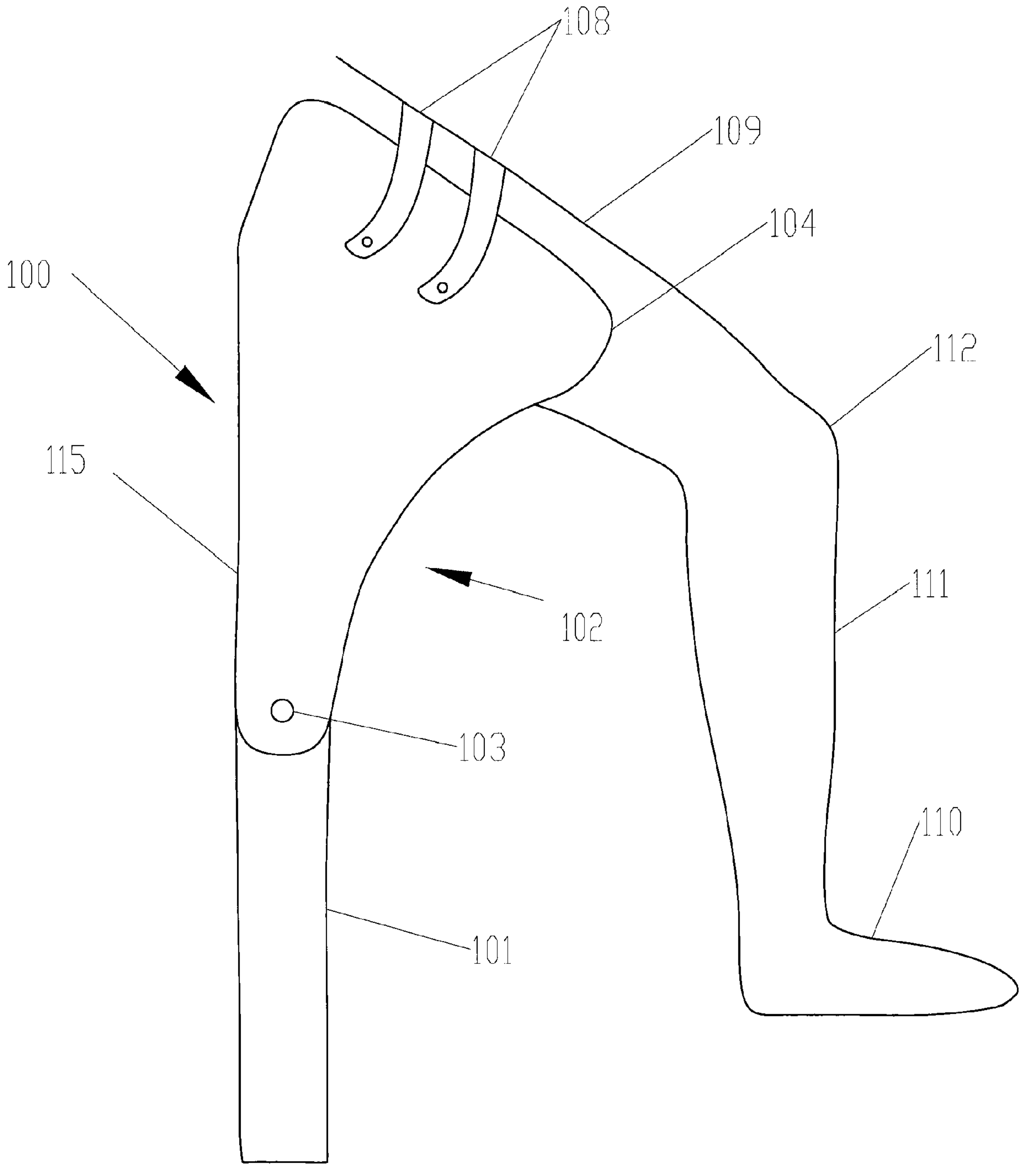
FIG. 5 depicts an embodiment of the walking assist device with a set of straps, which wrap around the person's thigh.
Figure 20:
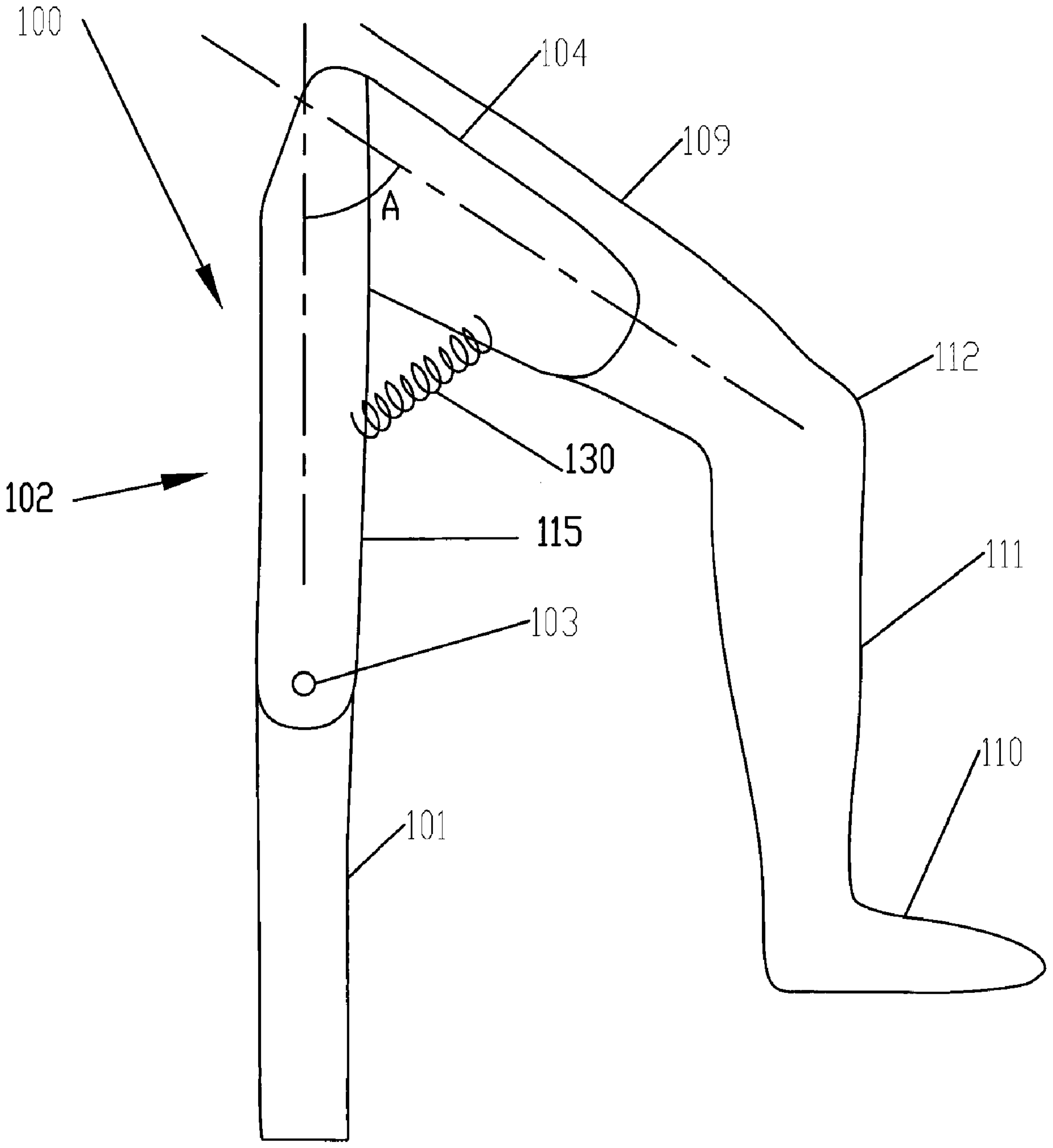
FIG. 20 depicts another embodiment of a walking assist device with a spring mounted between the thigh support and the thigh link.

In some embodiments, as shown in FIG. 3, thigh support 104 rotates slightly relative to thigh link 115 during walking. In some embodiments, the relative motion between thigh support 104 and thigh link 115 has at least one degree of freedom. Angle A, shown in FIG. 3, represents an example of this rotation in the sagittal plane. This slight motion might be needed for some patients to feel less constraint during locomotion. In some other embodiments, as shown in FIG. 4, the relative motion between thigh support 104 and thigh link 115 is configured to have at least one degree of freedom represented by arrow 113, which corresponds to an axis of rotation about the center line along thigh support 104 that approximately parallels the center line along the person's thigh 109. To create further comfort, in some embodiments as shown in FIG. 20, the mechanism between thigh support 104 and thigh link 115 is spring loaded. In one embodiment, spring 130 mounted between thigh support 104 and thigh link 115 to provide some compliancy between the thigh support 104 and the rest of the system. In some embodiments, as shown in FIG. 5, walking assist device 100 further comprises a set of straps 108, which are attached to thigh support 104 and which wrap around the person's thigh 109 to fix thigh support 104 to the person's thigh 109.

Figure 6:
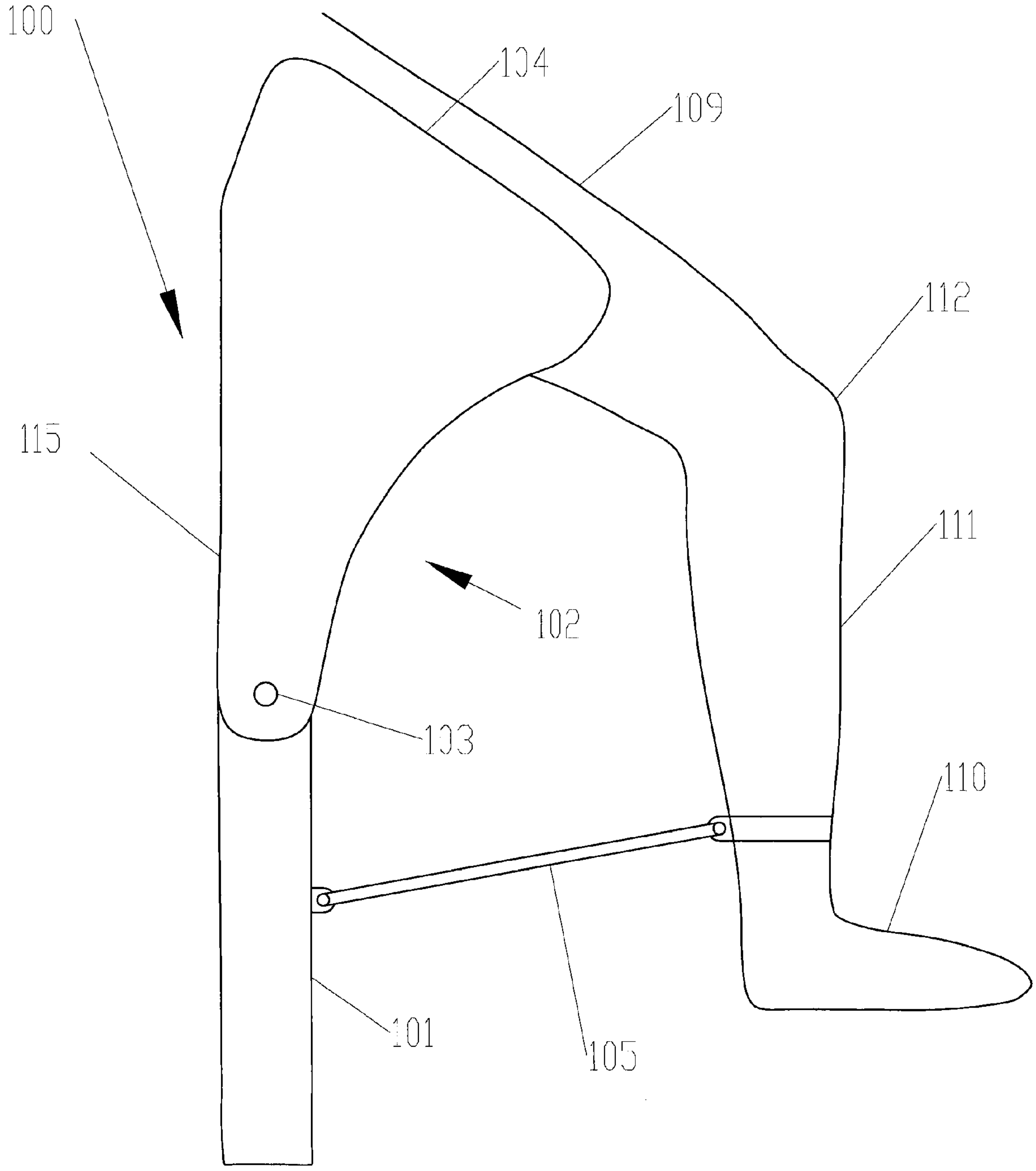
FIG. 6 depicts another embodiment of a walking assist device with a connecting link.
Figure 7:
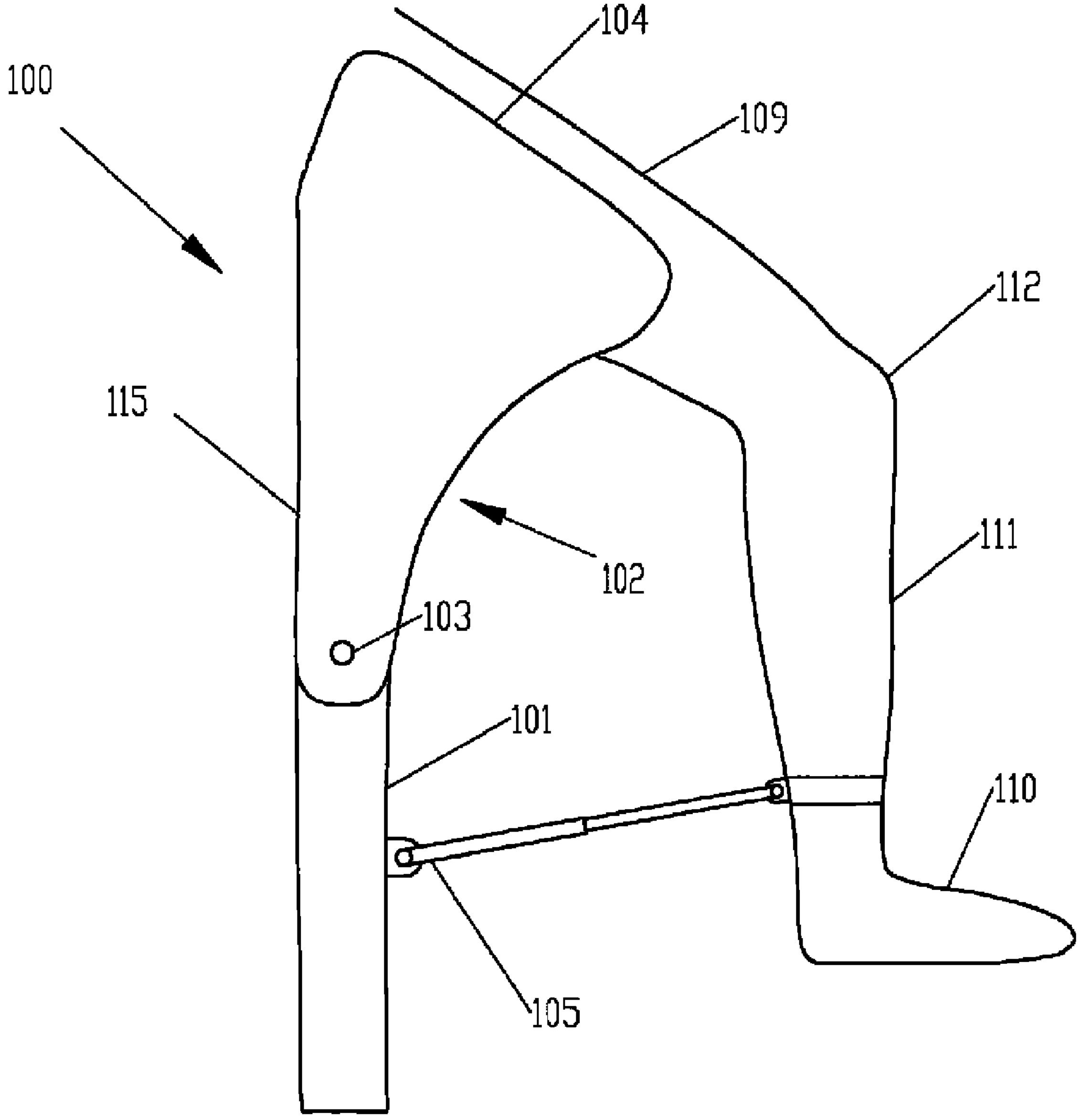
FIG. 7 depicts another embodiment of a walking assist device with an adjustable connecting link.
Figure 8:
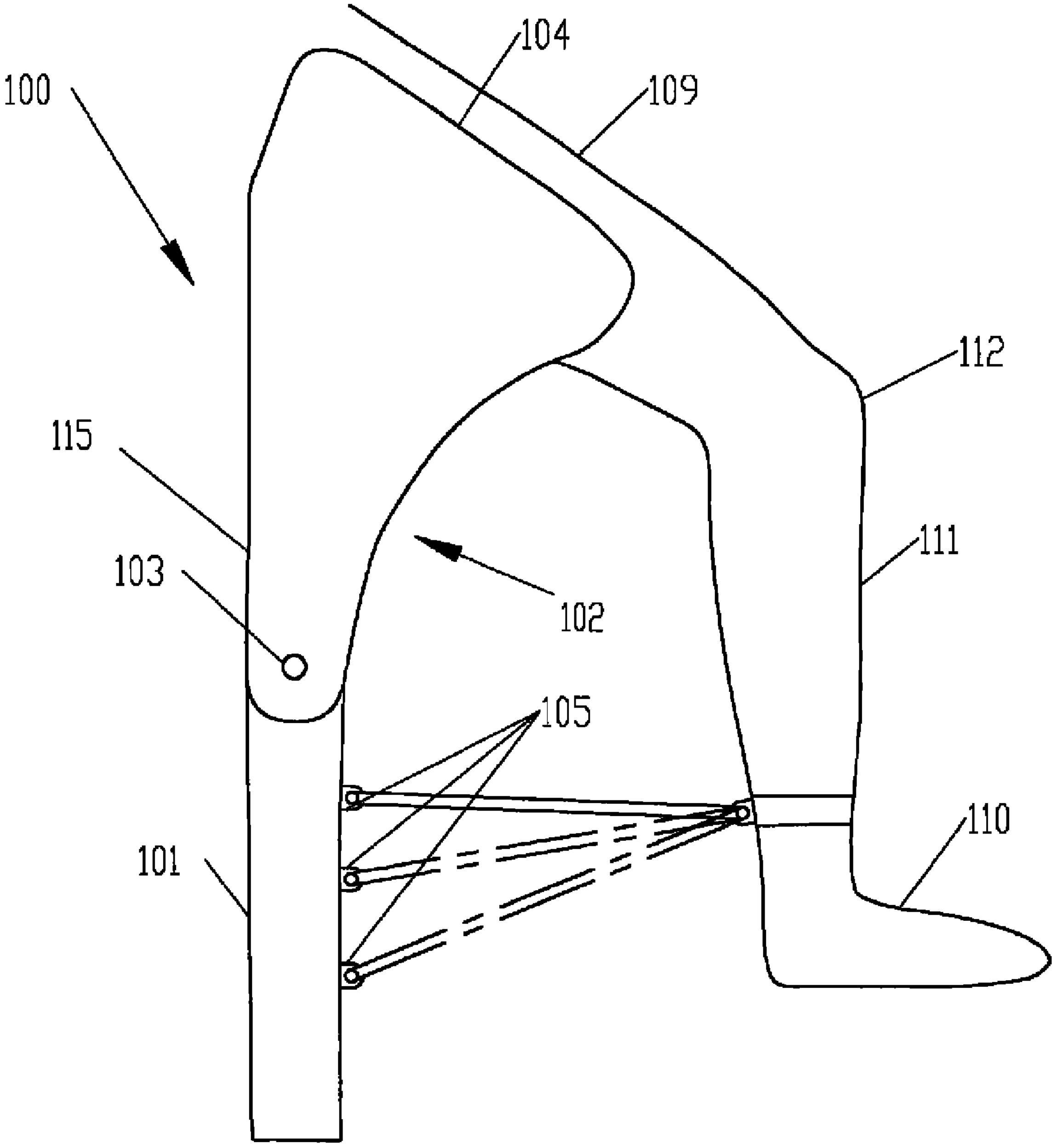
FIG. 8 depicts another embodiment of a walking assist device with a connecting link coupled with a shank link at an adjustable location.

In some embodiments, as shown in FIG. 6, walking assist device 100 further comprises a connecting link 105 which, in operation, couples shank link 101 with the person's leg 111 at a location below the person's knee 112. In some embodiments, as shown in FIG. 6, connecting link 105 is a rigid component. In some embodiments, connecting link 105 is a compliant component to create more comfort for the person. In some embodiments, as shown in FIG. 7, connecting link 105 has an adjustable length. In some embodiments, as shown in FIG. 8, connecting link 105 is coupled with shank link 101 at a location that is adjustable. This link provides an extra level of security or stability of the person's leg.

Figure 9:
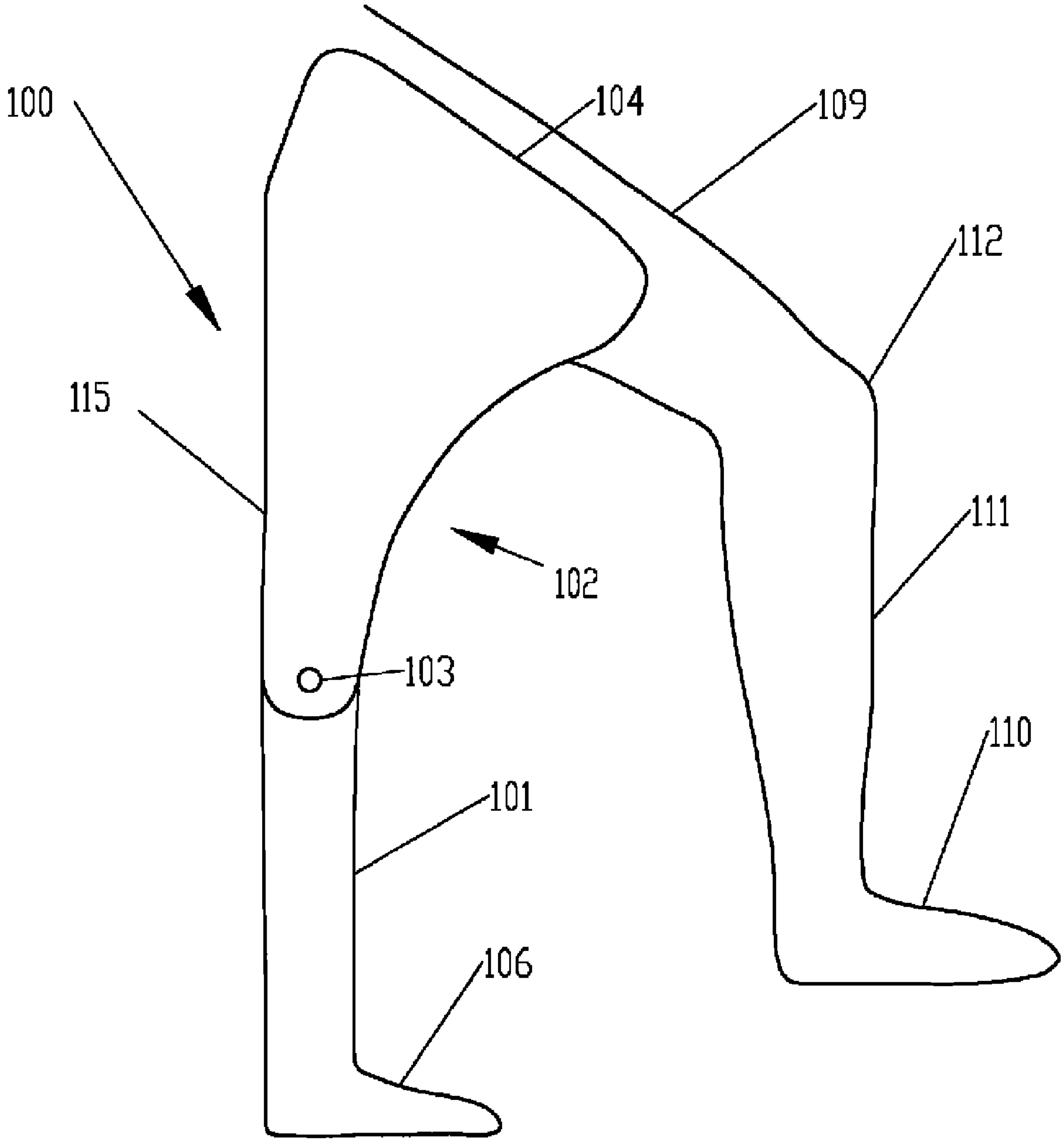
FIG. 9 depicts another embodiment of a walking assist device with an artificial foot.
Figure 10:
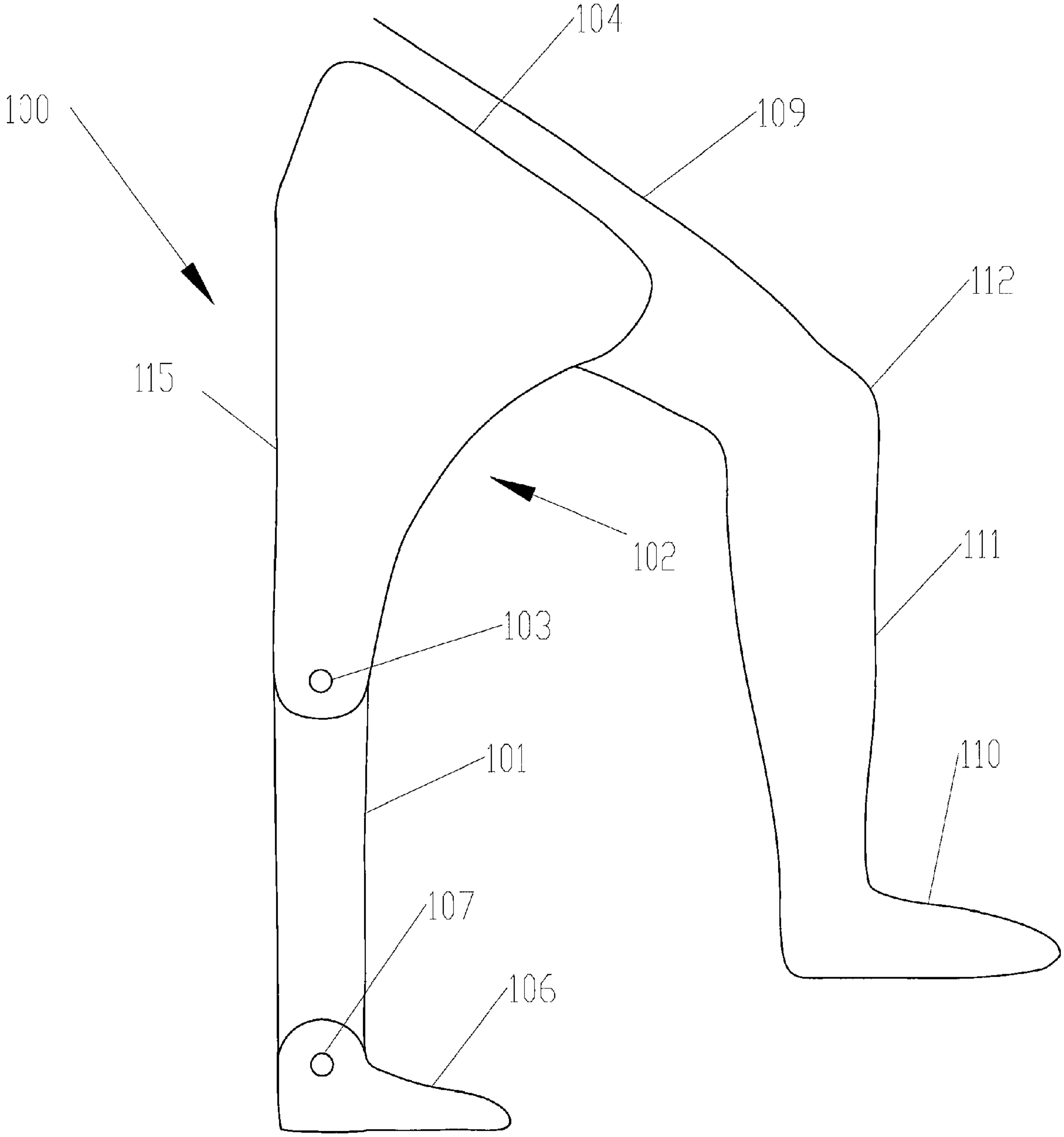
FIG. 10 depicts another embodiment of a walking assist device with an ankle joint between its shank link and an artificial foot.

In some embodiments, as shown in FIG. 9, walking assist device 100 further comprises an artificial foot 106 coupled to shank link 101. In some embodiments, as shown in FIG. 10, walking assist device 100 further comprises an ankle joint 107 between shank link 101 and artificial foot 106.

Figure 11:
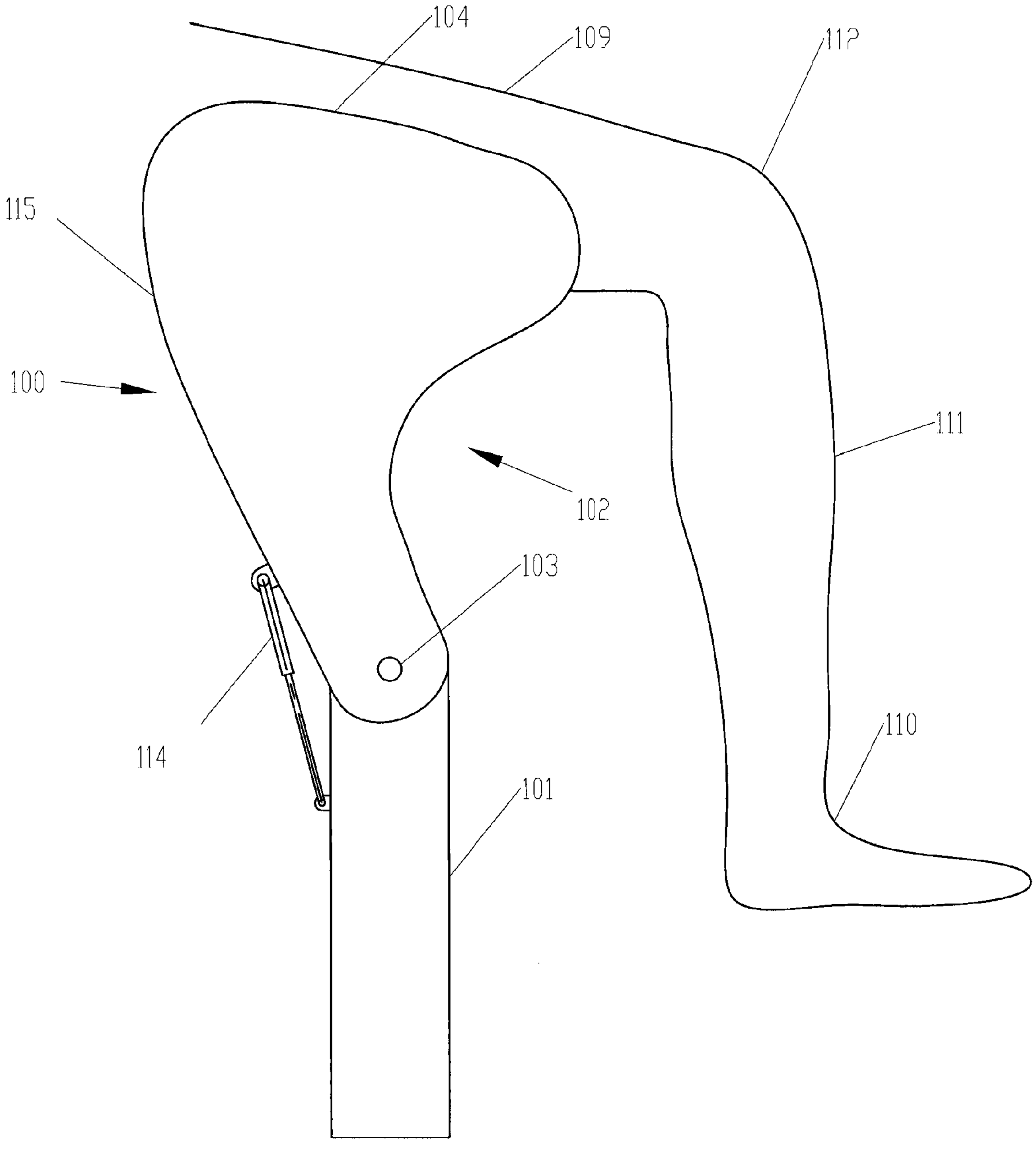
FIG. 11 depicts another embodiment of a walking assist device with a torque generator.
Figure 21:
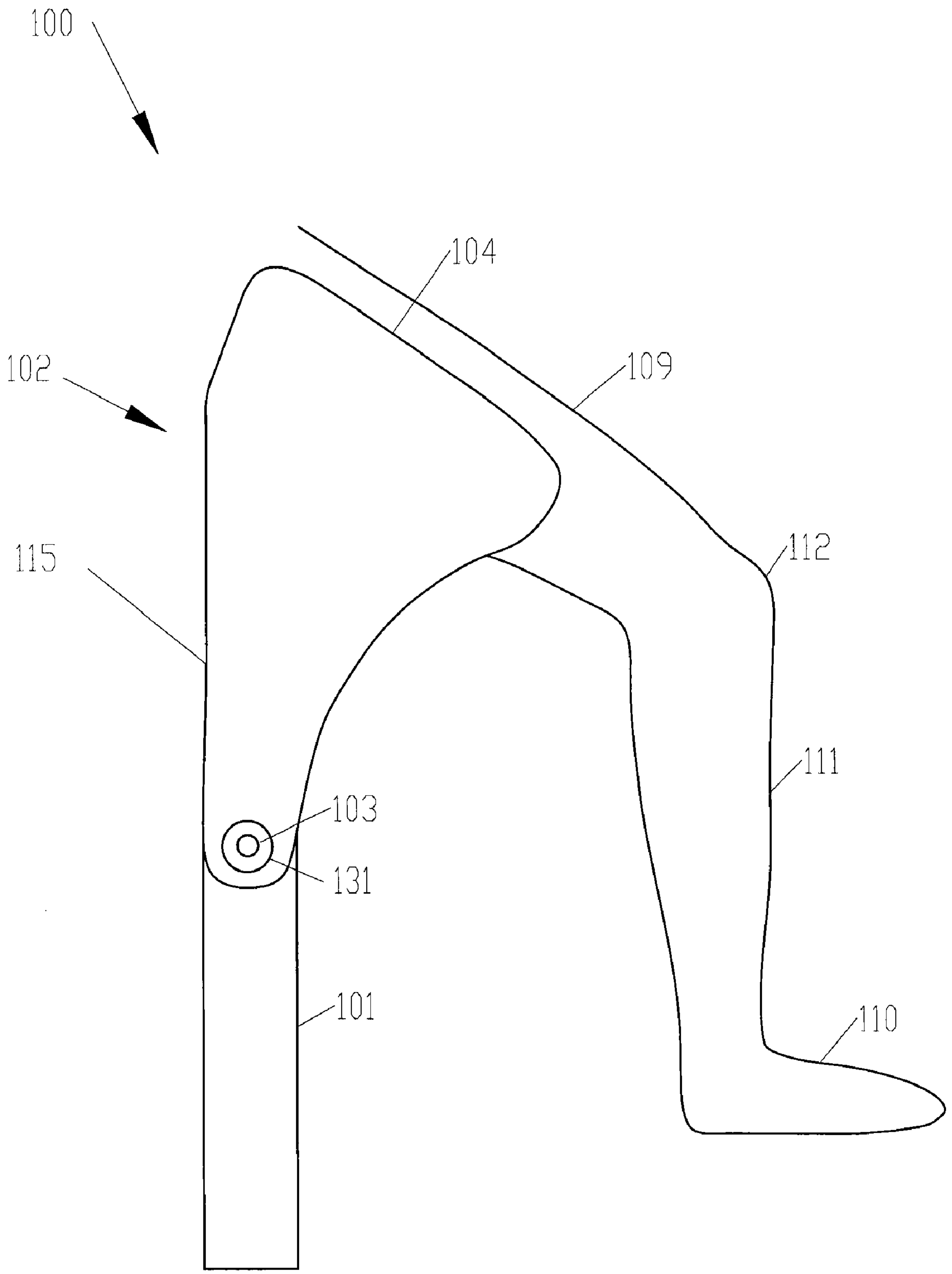
FIG. 21 depicts another embodiment of a walking assist device with the knee mechanism powered by a motor.

In some embodiments, as shown in FIG. 11, knee mechanism 103 may be hydraulically damped to be resistant to the movement of shank link 101 with respect to thigh member 102 when shank link 101 is in contact with the ground, and then to be less resistant to this motion when shank link 101 is not in contact with the ground. In some embodiments, as shown in FIG. 21, knee mechanism 103 is powered by a motor 131 to assist in ambulating.

In some embodiments, walking assist device 100 (as shown in FIG. 11) comprises a torque generator 114, which is configured to allow flexion of knee mechanism 103 during swing phase and to resist flexion of knee mechanism 103 during stance phase, thereby allowing walking assist device 100 to bear the person's weight and transfer the forces (e.g., the person's weight) to the ground.

In some embodiments, torque generator 114 is a hydraulic torque generator. In accordance with some embodiments, torque generator 114 is a hydraulic piston cylinder where the motion of the piston relative to the cylinder creates hydraulic fluid flow into or out of the cylinder. In operation, the hydraulic fluid flow into or out of the cylinder may be controlled by a hydraulic valve. In some embodiments, torque generator 114 is a friction brake where one can control the resistive torque on knee mechanism 103 by controlling the friction torque. In other embodiments, torque generator 114 is a viscosity-based friction brake where one can control the resistive torque on knee mechanism 103 by controlling the viscosity of the fluid. In other embodiments, torque generator 114 is a Magnetorheological Fluid Device where one can control the resistive torque on knee mechanism 103 by controlling the viscosity of the Magnetorheological Fluid. One skilled in the art realizes that any of the above devices can be mounted in the invention to function in the same way as the hydraulic damper shown in FIG. 11.

Knee mechanism 103, in some cases, is a locking joint that locks during the stance phase (i.e., does not bend) when vertical force is imposed on it. This type of knee mechanism is described in U.S. Pat. No. 3,863,274, which is incorporated herein by reference in its entirety for all purposes. Another example of a knee mechanism that locks during stance is described in U.S. Pat. No. 5,755,813, which is incorporated herein by reference in its entirety for all purposes. One experienced in the art can design all kinds of single-axis or polycentric knee mechanisms that lock or damp during stance.

Figure 12:
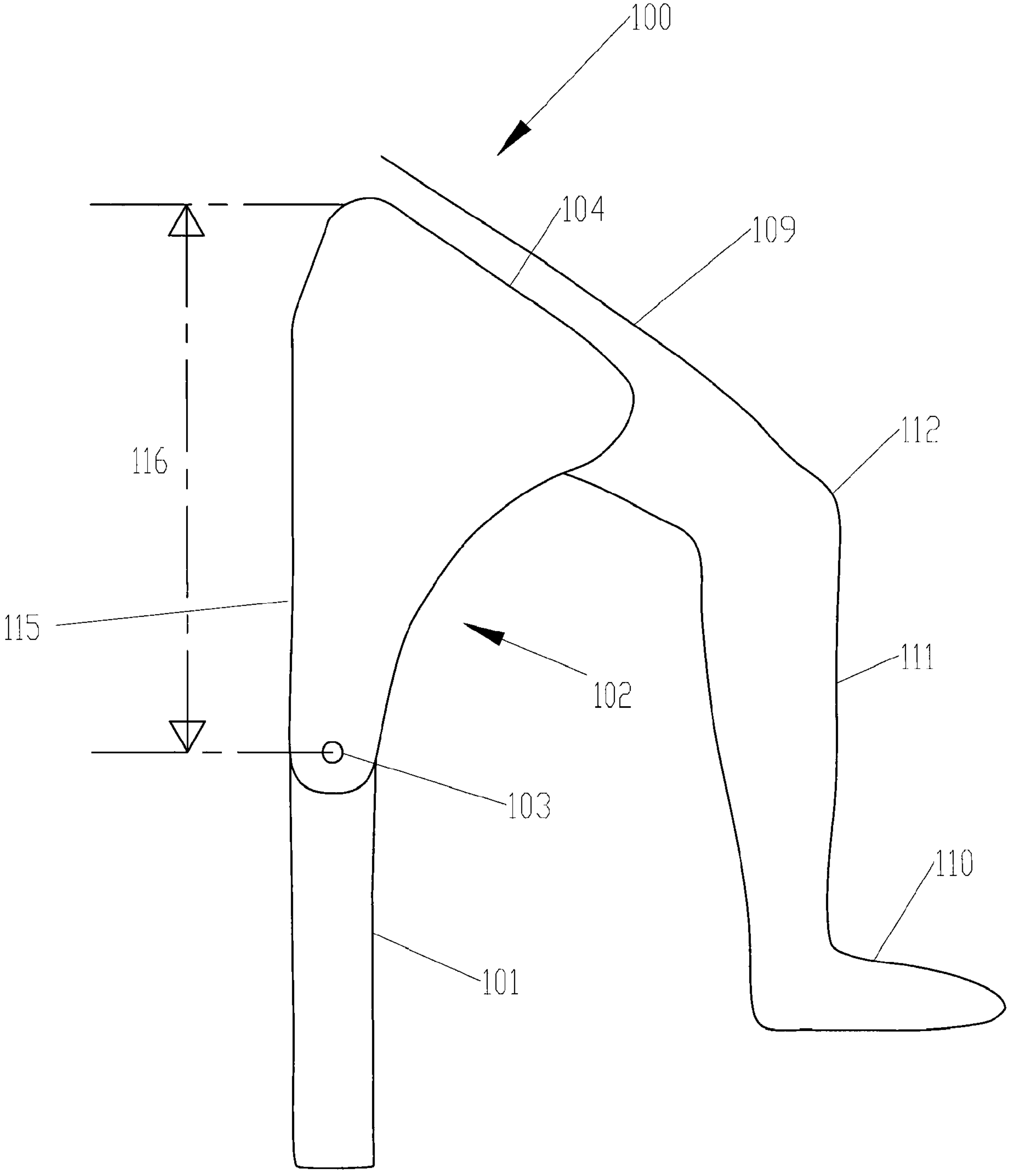
FIG. 12 depicts another embodiment of a walking assist device with a thigh member that has a fixed length.
Figure 13:
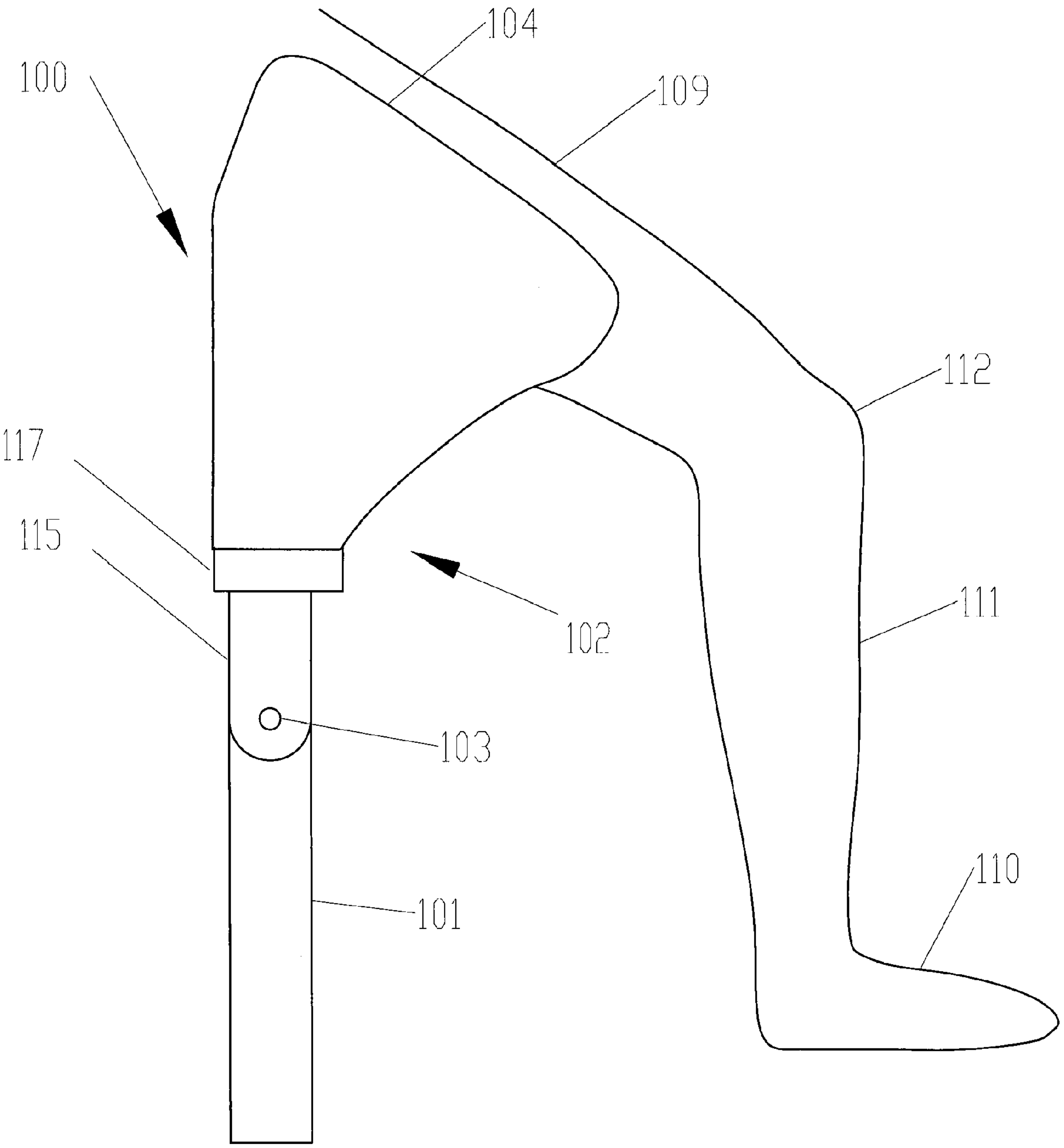
FIG. 13 depicts another embodiment of a walking assist device with a thigh link and thigh support coupled together through a compliant element.
Figure 14:
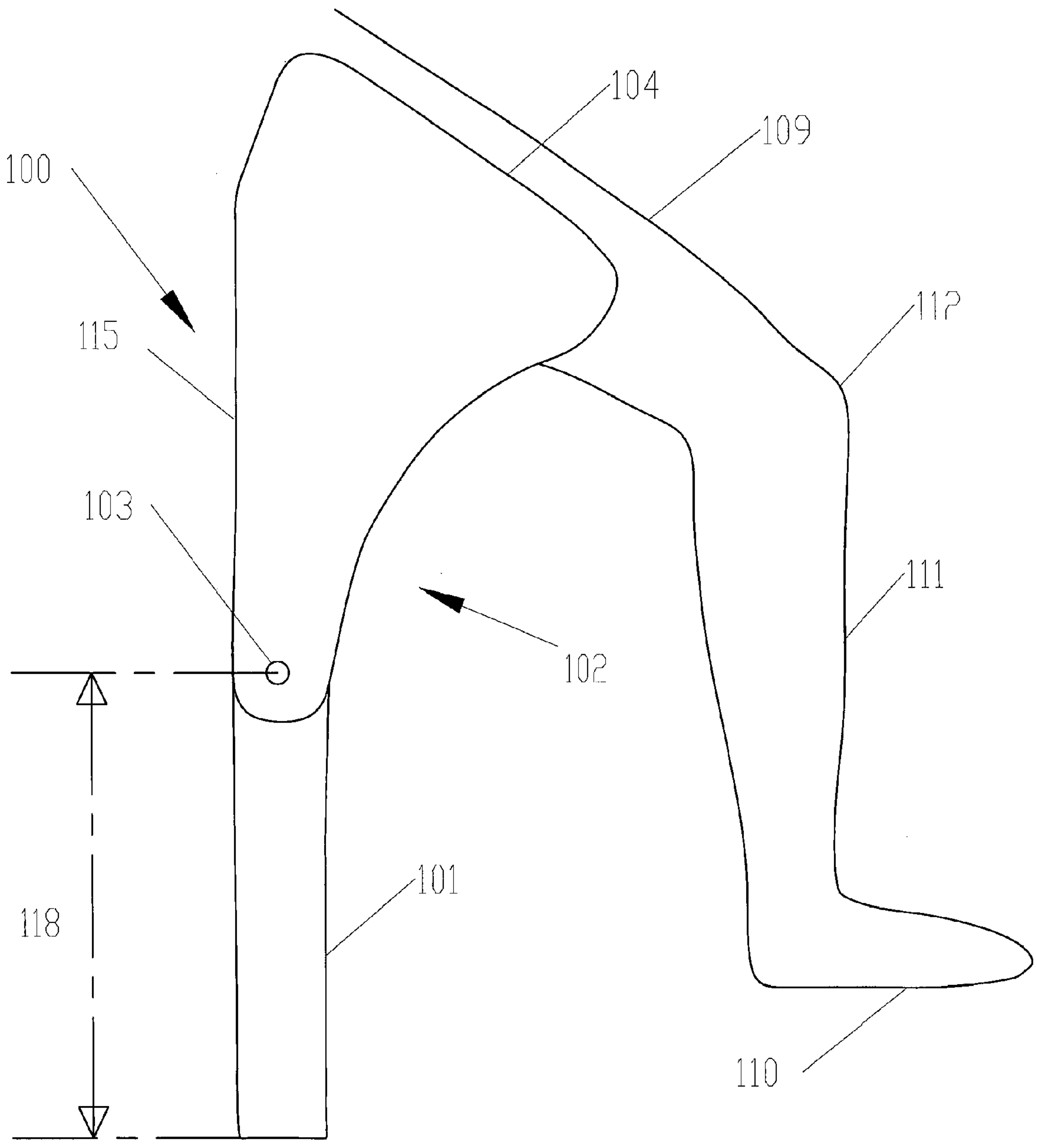
FIG. 14 depicts another embodiment of a walking assist device with a shank link that has a fixed length.
Figure 15:
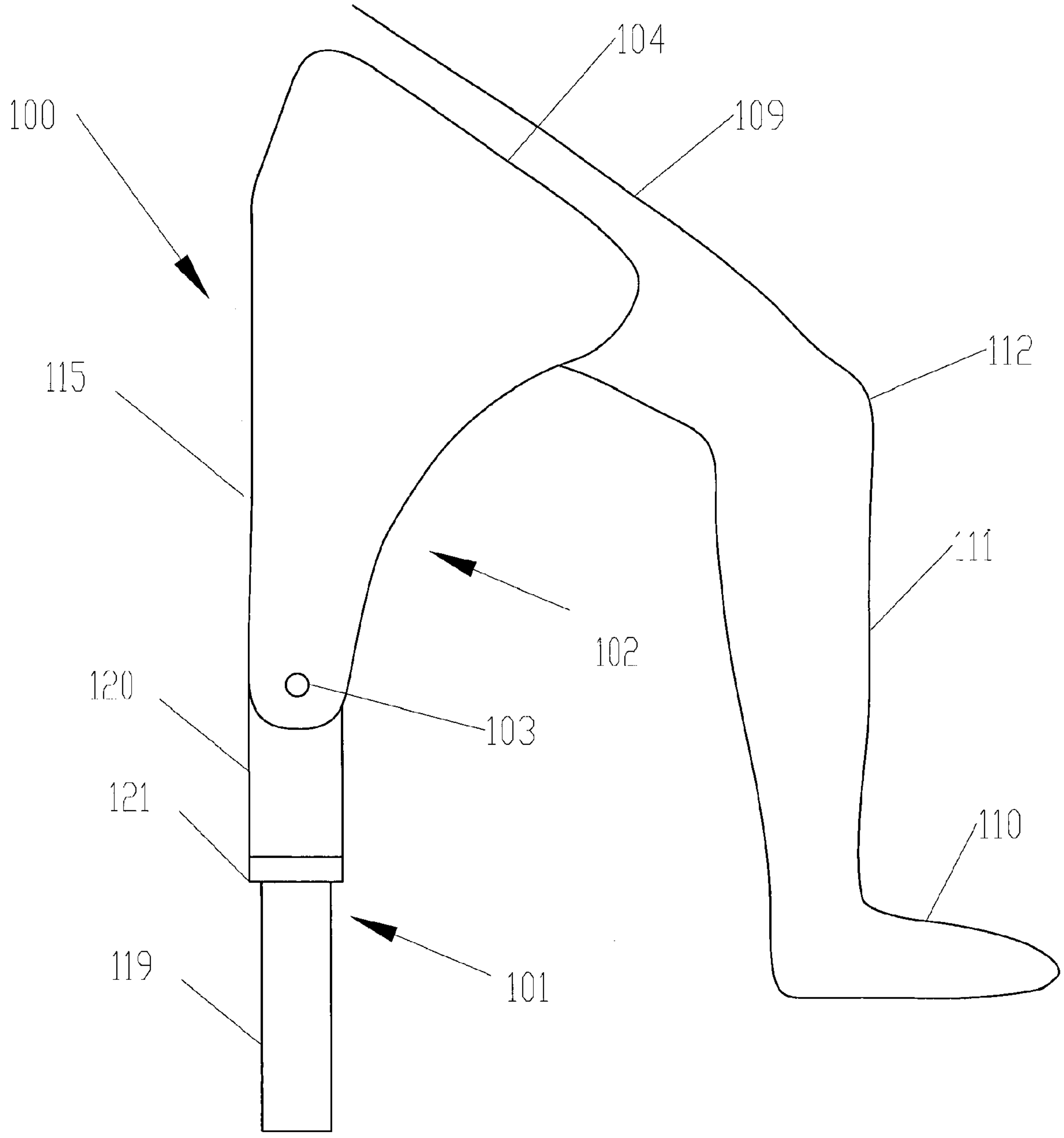
FIG. 15 depicts another embodiment of a walking assist device with a shank link that has at least two components coupled together through a compliant element.

In some embodiments, as shown in FIG. 12, thigh member 102 will have a fixed length 116. In some embodiments, thigh member 102 will have an adjustable length 116 to fit various individuals. In some embodiments, as shown in FIG. 13, thigh member 102 comprises thigh link 115 and thigh support 104 coupled together through a compliant element 117 to absorb and filter shock forces during stance phase. In some embodiments, as shown in FIG. 14, shank link 101 will have a fixed length 118. In some embodiments, shank link 101 will have an adjustable length 118 to fit various individuals. In some embodiments, as shown in FIG. 15, shank link 101 comprises at least two components 119 and 120 coupled together through a compliant element 121 to absorb and filter shock forces during stance phase.

Figure 16:
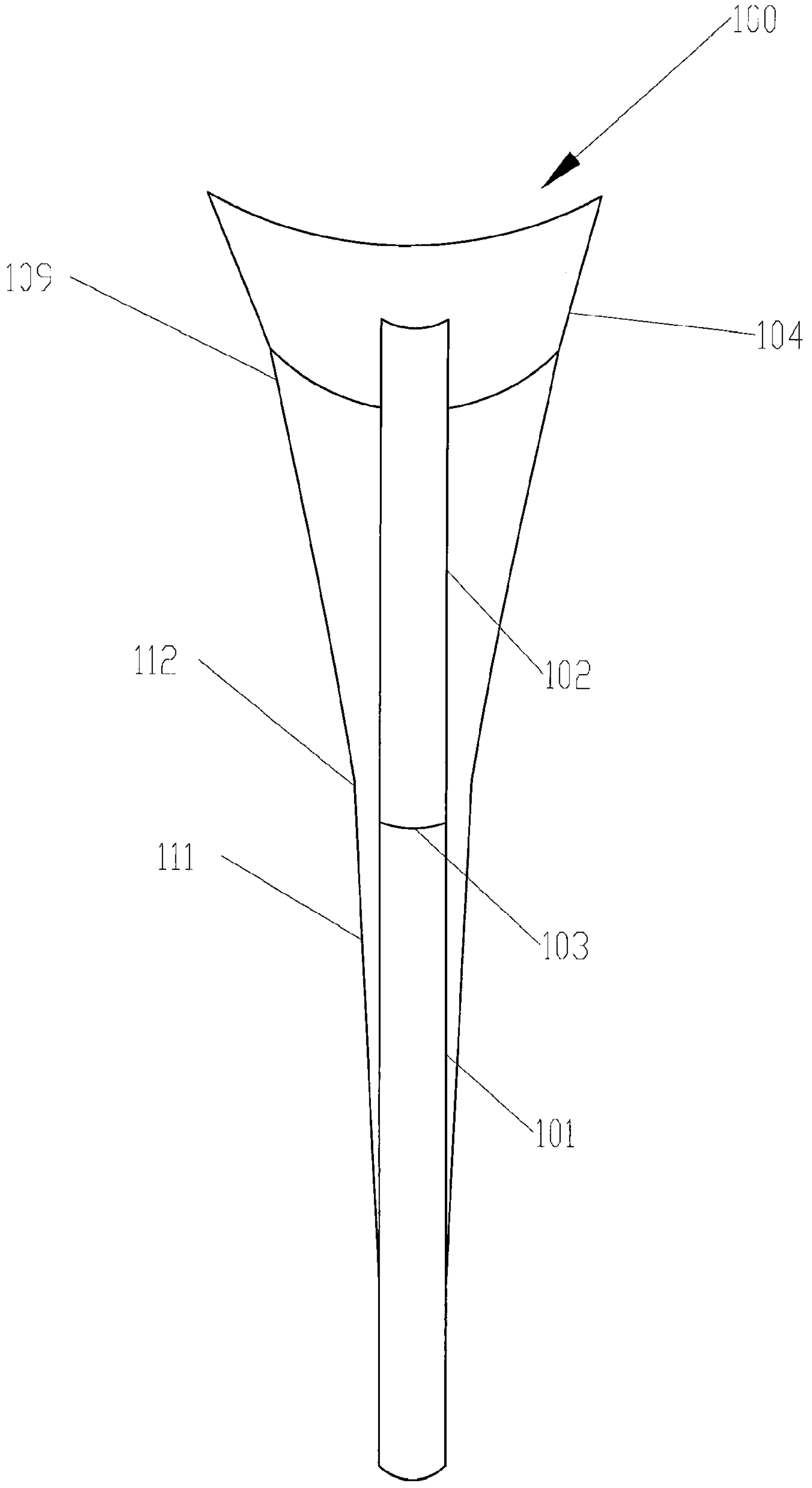
FIG. 16 depicts another embodiment of a walking assist device that is configured to be located behind the person's leg.
Figure 17:
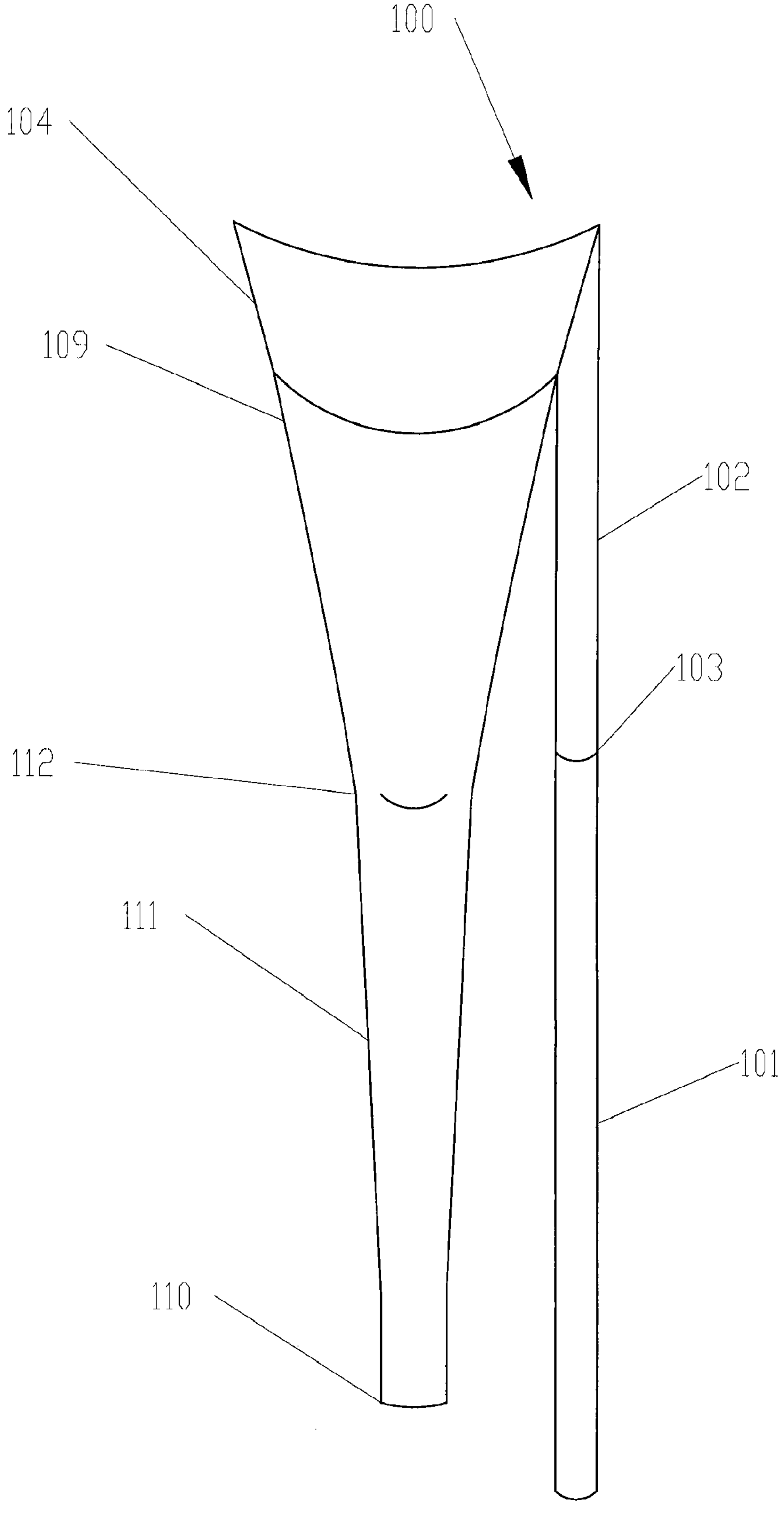
FIG. 17 depicts another embodiment of a walking assist device that is configured to be located to the side of the person's leg.

In some embodiments, as shown in FIG. 16, walking assist device 100 is located behind the person's leg 111. In some other embodiments, as shown in FIG. 17, walking assist device 100 is configured to be located to the side of the person's leg 111.

Figure 18:
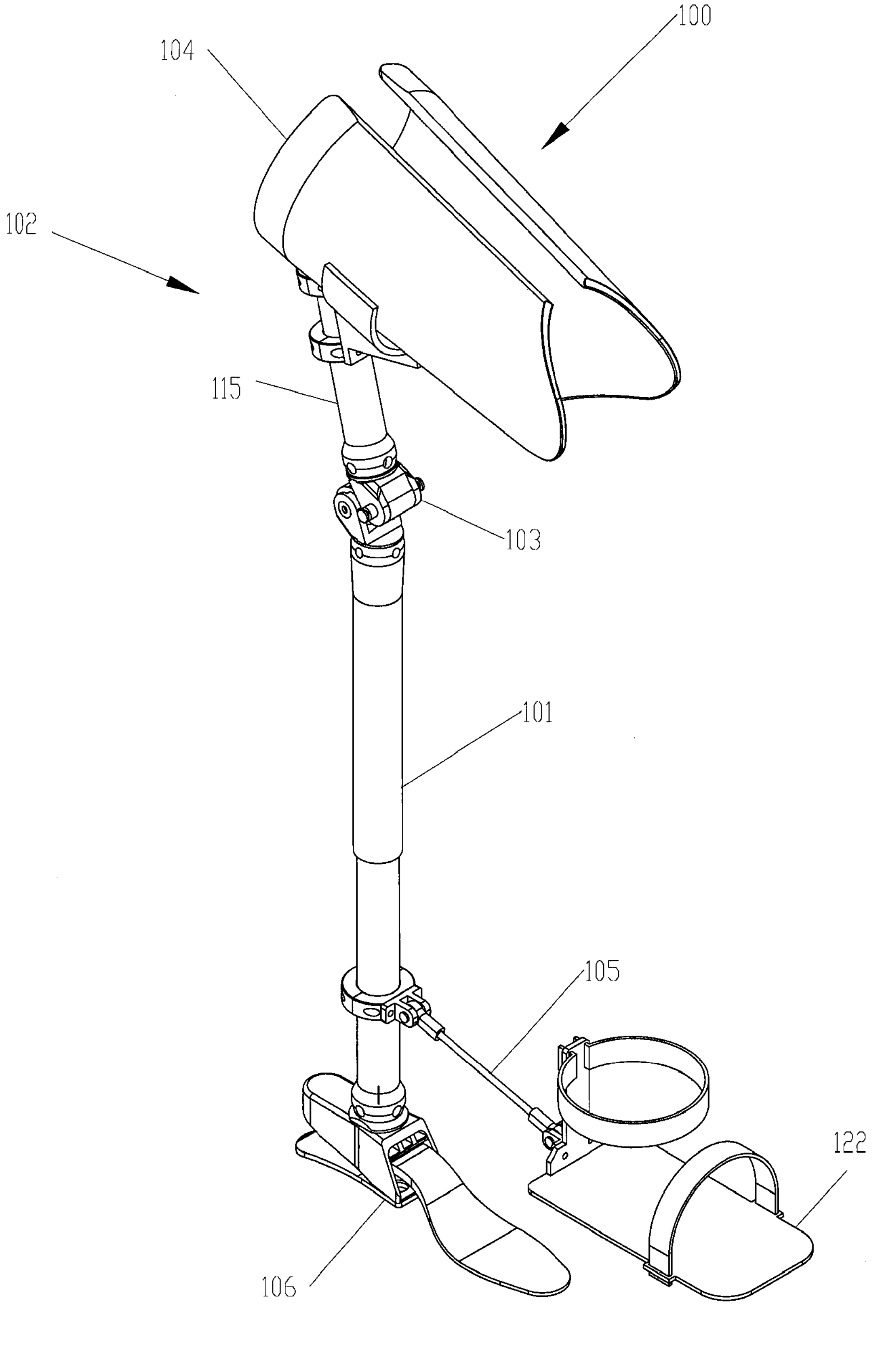
FIG. 18 is an isometric view of an exemplary walking assist device.
Figure 19:
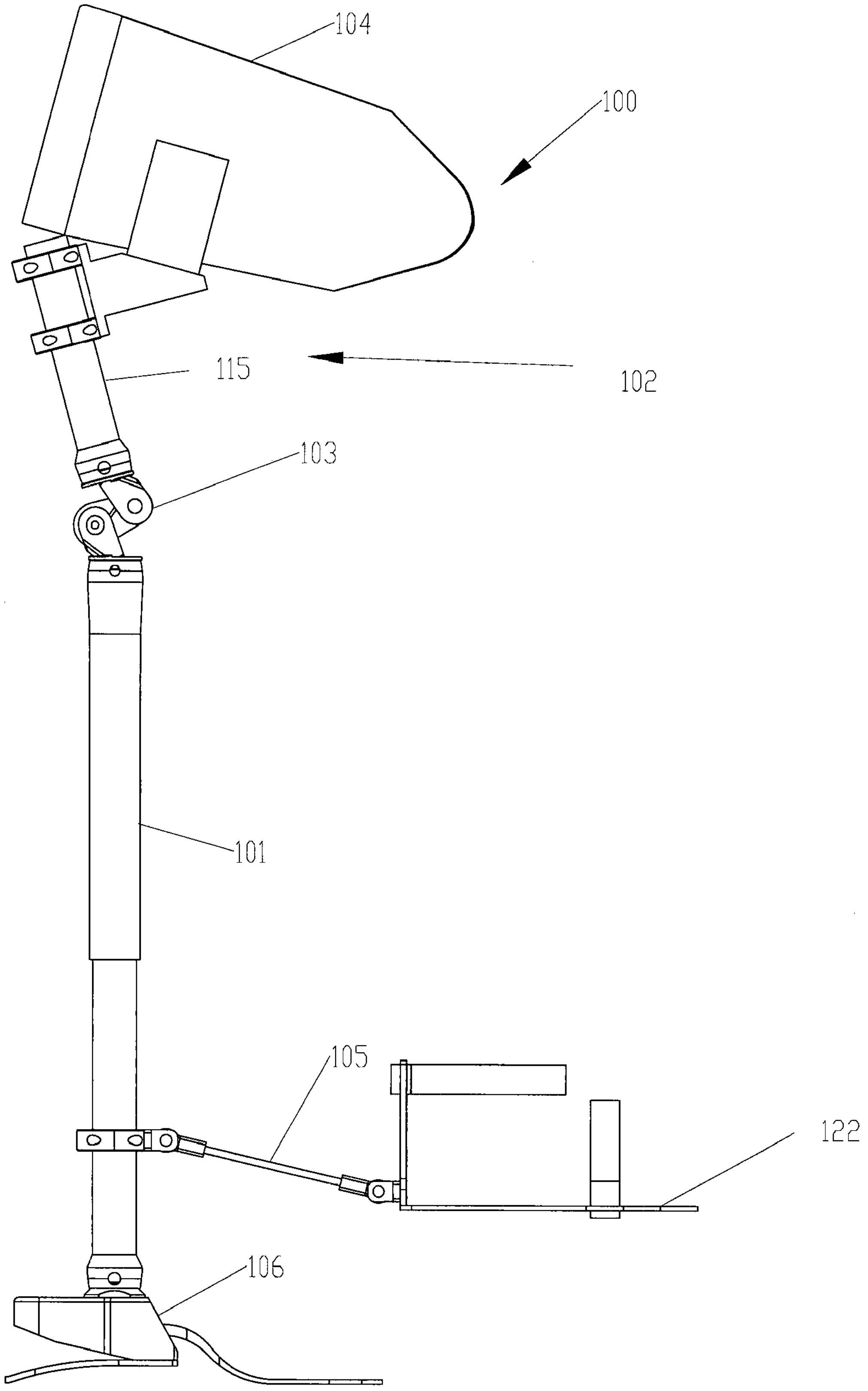
FIG. 19 is a side view of the walking assist device depicted in FIG. 18.

In accordance with an embodiment of the present invention, FIGS. 18 and 19 are drawings illustrating a walking assist device 100, which was built for evaluation. Walking assist device 100 comprises a shank link 101 and a thigh member 102 rotatably connected to each other at a knee mechanism 103. Thigh member 102 further comprises a thigh link 115 and a thigh support 104, which is in contact with the person's thigh. Thigh link 115 and shank link 101 are made of extruded aluminum tubes. Artificial foot 106, with a spring action, is coupled to shank link 101. Connecting link 105 couples shank link 101 to the person's leg at a location below the person's knee. In particular, connecting link 105 couples shank link 101 to foot support 122, which can be attached to the person's foot.

In operation when walking assist device 100 is in contact with the ground (i.e., stance phase) through its shank link 101, knee mechanism 103 will be locked to resist the motion of shank link 101 relative to thigh member 102, thereby preventing the person's foot from contacting the ground and reducing the ground reaction force entering the person's foot. Knee mechanism 103 in this case is a locking joint that locks (i.e., does not bend) when force is imposed on it. As mentioned above, this type of knee mechanism is described in U.S. Pat. No. 3,863,274, which is incorporated herein by reference in its entirety for all purposes. Another example of a knee mechanism that locks during stance is described in U.S. Pat. No. 5,755,813, which is incorporated herein by reference in its entirety for all purposes. One experienced in the art can design all kinds of single-axis or polycentric knee mechanisms that lock or damp during stance.

Although various exemplary embodiments have been described, it will be appreciated by persons skilled in the art that numerous variations and/or modifications may be made to the described device as specifically shown here without departing from the spirit or scope of that broader disclosure. The various examples are, therefore, to be considered in all respects as illustrative and not restrictive. In general, the invention is only intended to be limited by the scope of the following claims.

We claim:

1. A walking assist device to be worn on a person's leg, the device comprising:

a shank link;

a thigh member including a thigh support, which is in contact with the person's thigh when the device is worn on the person's leg, and a thigh link connected to the thigh support; and a knee mechanism that rotatably connects said shank link to the thigh link of said thigh member, with the shank link only being connected to the thigh support through the knee mechanism and the thigh link, wherein:

when said shank link is in contact with the ground, said knee mechanism is configured to resist the rotation of said shank link relative to said thigh member to prevent the person's foot from contacting the ground and to reduce ground reaction force entering the person's foot.

2. The walking assist device of claim 1, wherein, when said shank link is not in contact with the ground, said knee mechanism's resistance to the rotation of said shank link relative to said thigh member is less than said knee mechanism's resistance when said shank link is in contact with the ground.

3. The walking assist device of claim 1, wherein the orientation of said thigh link relative to said thigh support is fixed.

4. The walking, assist, device of claim 1, wherein the orientation of said thigh link relative to said thigh support is adjustable.

5. The walking assist device of claim 1, wherein said thigh support is rigidly connected to the person's thigh, preventing relative motion between said thigh support and the person's thigh when the device is worn on the person's leg.

6. The walking assist device of claim 1, wherein said thigh support rotates slightly relative to said thigh link during walking.

7. The walking assist device of claim 6, wherein the relative motion between said thigh support and said thigh link has at least one degree of freedom.

8. The walking assist device of claim 6, wherein said relative motion between said thigh support and said thigh link is provided by a spring.

9. The walking assist device of claim 1, further comprising straps, which are attached to said thigh support and wrap around the person's thigh to fix said thigh, support to the person's thigh when the device is worn on the person's leg.

10. The walking assist device of claim 1 further comprising:

a connecting link coupling said shank link with the person's leg at a location below the person's knee and above the person's ankle when the device is worn on the person's leg.

11. The walking assist device of claim 10, wherein said connecting link is a rigid component.

12. The walking assist device of claim 10, wherein said connecting link is a compliant component.

13. The walking assist device of claim 10, wherein said connecting link as an adjustable length.

14. The walking assist device of claim 10, wherein said connecting link is coupled with said shank link at an adjustable location.

15. The walking assist device of claim 1 further comprising an artificial foot coupled to said shank link.

16. The walking assist device of claim 15 further comprising an ankle joint located between said shank link and said artificial foot.

17. The walking assist device of claim 1, wherein said knee mechanism is hydraulically damped to be resistant to the movement of said shank link with respect to said thigh member when said shank link is in contact with the ground, and then to be less resistant to this motion when said shank link is not in contact with the ground.

18. The walking assist device of claim 1, further comprising:

a torque generator configured to allow flexion of said knee mechanism during swing phase and to resist flexion of said knee mechanism during stance phase to allow the transfer of forces to the ground, wherein said shank link is not in contact with the ground in said swing phase, and wherein said shank link is in contact with the ground in said stance phase.

19. The device of claim 18, wherein said torque generator is a hydraulic piston cylinder, wherein the hydraulic piston cylinder's resistive force can be controlled by controlling the fluid flow through a hydraulic valve.

20. The device of claim 18, wherein said torque generator is selected from a group consisting of friction brakes, viscosity-based friction brakes, and Magnetorheological Fluid Devices.

21. The walking assist device of claim 1, wherein said knee mechanism is powered by a motor to assist in ambulating.

22. The walking assist device of claim 1, wherein said knee mechanism comprises at least one rotary joint allowing rotary motion between said shank link and said thigh member during the swing phase when said shank link is not in contact with the ground.

23. The walking assist device of claim 1, wherein said thigh member has a fixed length.

24. The walking assist device of claim 1, wherein said thigh member has an adjustable length.

25. The walking assist device of claim 1, wherein said thigh member comprises a thigh support and thigh, link coupled together through a compliant element to absorb and filter shock forces during stance phase when the shank link is in contact with the ground.

26. The walking assist device of claim 1, wherein said shank link has a fixed length.

27. The walking assist device of claim 1, wherein said shank link has an adjustable length.

28. The walking assist device of claim 1, wherein said shank link comprises at least two components coupled together through a compliant element to absorb and filter shock forces during stance phase when the shank link is in contact with the ground.

29. The walking assist device of claim 1, wherein said shank link and thigh member are located behind the person's leg when the device is worn on the person's leg.

30. The walking assist device of claim 1, wherein said shank link and thigh member are located to the side of the person's leg when the device is worn on the person's leg.

31. A walking assist device to be worn on a person's leg, the device comprising:

a shank link;

a thigh member, which is in contact with the person's thigh when the device is worn on the person's leg; and a knee mechanism that rotatably connects said shank link to said thigh member, wherein said knee mechanism comprises a four-bar mechanism allowing rotary, motion between said shank link and said thigh member during the swing phase when said shank link is not in contact with the ground and wherein:

when said shank link is in contact with the ground, said knee mechanism is configured to resist the rotation of said shank link relative to said thigh member to prevent the person's foot from contacting the ground and to reduce ground reaction force entering the person's foot.

32. A walking assist device to be worn on a person's leg, the device comprising:

a shank link;

a thigh member, which is in contact with the person's thigh when the device is worn on the person's leg;

a knee mechanism that rotatably connects said shank link to said thigh member, wherein:

when said shank link is in contact with the ground, said knee mechanism is configured to resist the rotation of said shank link relative to said thigh member to prevent the person's foot from contacting the ground and to reduce ground reaction forces entering the person's foot;

wherein, when said shank link is not in contact with the ground, said knee mechanism's resistance to the rotation of said shank link relative to said thigh member is less than said knee mechanism's resistance when said shank link is in contact with the ground; and a connecting link coupling said shank link with the person's leg at a location below the person's knee and above the person's ankle when the device is worn on the person's leg.

33. The walking assist device of claim 32, wherein the thigh member includes a thigh support, which is in contact with the person's thigh when the device is worn on the person's leg, and a thigh link connected to the thigh support, with the shank link only being connected to the thigh support through the knee mechanism and the thigh link.

* * * * *